(12) United States Patent
Motheram

(10) Patent No.: US 7,985,733 B1
(45) Date of Patent: *Jul. 26, 2011

(54) BUFFER-BASED METHOD FOR PREPARING BIVALIRUDIN DRUG PRODUCT

(75) Inventor: Rajeshwar Motheram, Dayton, NJ (US)

(73) Assignee: The Medicines Company, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/683,045

(22) Filed: Jan. 6, 2010

(51) Int. Cl.
*A61K 38/36* (2006.01)

(52) U.S. Cl. .................................................. 514/13.7

(58) Field of Classification Search .................. None
See application file for complete search history.

(56) References Cited

U.S. PATENT DOCUMENTS

| | | | |
|---|---|---|---|
| 5,196,404 | A | 3/1993 | Maraganore et al. |
| 5,240,913 | A | 8/1993 | Maraganore et al. |
| 5,268,296 | A | 12/1993 | Maschler et al. |
| 5,425,936 | A | 6/1995 | Maraganore et al. |
| 5,433,940 | A | 7/1995 | Maraganore et al. |
| 5,661,001 | A | 8/1997 | Grossenbacher et al. |
| 5,691,311 | A | 11/1997 | Maraganore et al. |
| 6,274,553 | B1 | 8/2001 | Furuya et al. |
| 7,598,343 | B1 | 9/2009 | Krishna et al. |
| 7,582,727 | B1 | 10/2009 | Krishna et al. |
| 2005/0250704 | A1 | 11/2005 | Bassarab et al. |
| 2006/0246480 | A1 | 11/2006 | Caprioli |
| 2006/0292607 | A1 | 12/2006 | Caprioli |
| 2007/0093423 | A1 | 4/2007 | Tovi et al. |
| 2007/0116729 | A1 | 5/2007 | Palepu |
| 2008/0287650 | A1 | 11/2008 | Tovi et al. |
| 2009/0062511 | A1 | 3/2009 | Palle et al. |
| 2009/0110679 | A1 | 4/2009 | Li et al. |
| 2009/0269422 | A1 | 10/2009 | Yu |
| 2010/0029916 | A1 | 2/2010 | Tovi et al. |
| 2010/0273982 | A1 | 10/2010 | Tovi et al. |

FOREIGN PATENT DOCUMENTS

| | | |
|---|---|---|
| CN | 101244043 | 8/2008 |
| WO | 2008/107729 | 9/2008 |
| WO | 2008109079 | 9/2008 |
| WO | 2009086062 | 7/2009 |
| WO | 2010075983 | 7/2010 |
| WO | 2010117725 | 10/2010 |

OTHER PUBLICATIONS

Chi et al. ("Physical Stability of Proteins in Aqueous Solution: Mechanism and Driving Forces in Nonnative Protein Aggregation," Pharmaceutical Research, 2003, 20, 1325-1336).*
Carpenter et al. ("Rational Design of Stable Lyophilized Protein Formulations: Some Practical Advice," Pharmaceutical Research, 1997, 14, 969-975).*
U.S. Appl. No. 12/180,550, filed Jul. 27, 2009, Krishna et al.
U.S. Appl. No. 12/563,821, filed Sep. 21, 2009, Palepu et al.
U.S. Appl. No. 12/545,062, filed Aug. 20, 2009, Palepu et al.
U.S. Appl. No. 12/545,036, filed Aug. 20, 2009, Palepu et al.
Angiomax® U.S. Prescribing Information, Dec. 6, 2005.
EMEA Publication 2005 (http://www.emea.europa.eu/humandocs/PDFs/ EPAR/angiox/103304en6.pdf).
M. Staples, *Pharm. Res.* 1992, 9:10, Suppl., S79 (BIOTEC 2049).
AHFS Fact Sheet-Angiomax®, Jul. 2007.
Material Safety Data Sheet for Angiomax® 2009 (http://angiomax.com/Files/Angiomax-MSDS.pdf).
Material Safety Data Sheet for Angiomax® 2000.
Material Safety Data Sheet for Angiomax® 2001.
D. Parkins et al., The Formulation of Biopharmaceutical Products, *PSTT* vol. 3, No. 4, Apr. 2000, pp. 129-137.
A.Wakankar & R.Borchardt, Formulation Considerations for Proteins Susceptible to Asparagine Deamidation and Aspartate Isomerization, *J. Pharm. Sci.*, vol. 95, No. 11, Nov. 2006, pp. 2321-2336.
FDA Label for Angiomax®, Dec. 15, 2000.
Amsberry et al., Compatability and Stability of Bivalirudin in IV Admixtures, *APPS Pharm. Sci.*, 1999, vol. 11, p. S1.
L.P. Stratton et al., Controlling Deamidation Rates in a Model Peptide: Effects of Temperature, Peptide Concentration, and Additives, *J. Pharm. Sci.*, vol. 90, No. 12, Dec. 2001, p. 2141-48.

* cited by examiner

*Primary Examiner* — Christina Bradley
(74) *Attorney, Agent, or Firm* — Frommer Lawrence & Haug LLP; Sandra Kuzmich; Russell A. Garman

(57) ABSTRACT

A method for preventing the formation of a bivalirudin precipitate during preparation of a pharmaceutical drug product comprising about 250 mg of bivalirudin, a dried bivalirudin drug product, and a concentrated liquid bivalirudin drug product. The method for preventing the formation of a bivalirudin precipitate comprises (i) preparing an aqueous solution comprising a buffer and a pH greater than the isoelectric point of bivalirudin; (ii) adding bivalirudin salt to the aqueous solution to form a bulk solution; (iii) transferring the bulk solution to one or more vessels; and (iv) drying the bulk solution. The buffer may have a $pK_a$ of about 4 to less than 7, and a pH greater than the isoelectric point of bivalirudin. The pH of the bulk solution may be maintained at a level greater than the isoelectric point of bivalirudin. Further, the bulk solution may have a final pH of about 4 to about 7.

17 Claims, No Drawings

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe

<400> SEQUENCE: 1
```

```
Phe Pro Arg Pro Gly Gly Gly Gly Asn Gly Asp Phe Glu Glu Ile Pro
1               5                   10                  15
Glu Glu Tyr Leu
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe

<400> SEQUENCE: 2

Phe Pro Arg Pro Gly Gly Gly Gly Asp Gly Asp Phe Glu Glu Ile Pro
1               5                   10                  15
Glu Glu Tyr Leu
            20
```

BUFFER-BASED METHOD FOR PREPARING BIVALIRUDIN DRUG PRODUCT

FIELD OF THE INVENTION

The present invention is generally directed towards a method for preventing the formation of a bivalirudin precipitate during the preparation of a pharmaceutical drug product comprising about 250 mg of bivalirudin. The method may comprise (i) preparing an aqueous solution comprising a buffer and a pH greater than the isoelectric point of bivalirudin; (ii) adding bivalirudin salt to the aqueous solution to form a bulk solution; (iii) transferring the bulk solution to one or more vessels; and (iv) drying the bulk solution. In certain embodiments, the aqueous and bulk solutions may be maintained at a pH greater than the isoelectric point of bivalirudin to prevent the formation of a bivalirudin precipitate. The buffer of the present invention may have a $pK_a$ of about 4 to less than 7. In certain embodiments, the bulk solution may have a final pH of about 4 to about 7. In additional embodiments, the bulk solution is transferred to provide about 250 mg of bivalirudin to each of the vessels. The present invention also generally relates to a dried bivalirudin drug product and a concentrated liquid bivalirudin drug product that are administered to a patient in need thereof.

BACKGROUND OF THE INVENTION

Thrombin is a serine protease that plays an essential role during blood clotting. Clotting is initiated when blood vessel walls are damaged and subendothelium proteins are released, inducing a cascade of events that includes the activation of platelets and conversion of prothrombin to thrombin. The activated platelets and thrombin recruit more platelets and propagate local inflammation through leukocyte and endothelial cell activations, fueling thrombosis. While thrombin is central to the formation of a thrombus early on, it continues to further activate platelets and inflammatory pathways. Thrombin is the most potent physiologic platelet agonist known.

Anticoagulants are substances that prevent blood clotting, and include the class of anticoagulants that are direct thrombin inhibitors. One such thrombin inhibitor is bivalirudin (Angiomax®), which directly inhibits thrombin by specifically binding to both its catalytic site and its anion-binding exosite. Angiomax® is FDA-approved to treat patients with unstable angina undergoing percutaneous transluminal coronary angioplasty (PTCA); to administer with the provisional use of glycoprotein IIb/IIIa inhibitor for use as an anticoagulant in patients undergoing percutaneous coronary intervention (PCI); and to treat patients with, or at risk of, heparin-induced thrombocytopenia (HIT) or heparin-induced thrombocytopenia and thrombosis syndrome (HITTS) undergoing PCI. Angiomax® Prescribing Information at 2. Angiomax® is intended for use with aspirin and has been studied only in patients concomitantly receiving aspirin. Id. Furthermore, Angiomax® (Angiox® in Europe) has received European approval for use as an anticoagulant in patients with heart attacks (so-called ST-segment elevation myocardial infarction (STEMI)) undergoing emergency heart procedures called primary PCI.

Angiomax® is delivered through intravenous administration and supplied as a sterile, lyophilized drug product in a single-use vial. Id. at 1, 4. Each single-use vial contains 250 mg of bivalirudin, 125 mg mannitol, and sodium hydroxide to adjust the pH to about 5-6 (equivalent of approximately 12.5 mg sodium). Id. When reconstituted with a sterile aqueous solution for injection, Angiomax® yields a clear to opalescent, colorless to slightly yellow solution. Id.

When Angiomax® was approved by FDA in December of 2000, it was prepared by a compounding process whereby a solution comprising sodium hydroxide ("NaOH solution") was added to a solution comprising bivalirudin salt ("bivalirudin solution") to form a compounding solution. The bivalirudin solution had a pH of between about 1.8 to about 2.8, and the addition of the NaOH solution resulted in a compounding solution that had a final pH of between about 5 and about 6. However, as the NaOH solution was added to the bivalirudin solution, the pH of the resulting compounding solution passed through the isoelectric point ("pI") of bivalirudin (about 3.6), where bivalirudin had limited solubility and a portion of bivalirudin precipitated as a dense material, forming a "gum-like" gel. Once bivalirudin gelled or became "gum-like," there was a significant delay as bivalirudin had to be re-dissolved. Such a delay extended production time while manufacturer operators tried to re-dissolve the "gum-like" bivalirudin. In addition, this compounding process also resulted in inconsistent and sometimes elevated levels of impurities such as $Asp^9$-bivalirudin as a result of localized sites of high pH in the compounding solution that were produced when the precipitate formed.

Currently, Angiomax® is prepared according to the process described in U.S. Pat. No. 7,598,343 ("the '343 patent"). The '343 patent teaches a process wherein the method of preparing pharmaceutical batch(es) or pharmaceutical formulation(s) of bivalirudin may comprise (1) dissolving bivalirudin salt in a solvent to form a bivalirudin solution; (2) efficiently mixing a pH-adjusting solution with the bivalirudin solution to form a compounding solution; and (3) removing the solvent from the compounding solution. See, e.g., '343 patent, col.6,1.61-col.12,1.9.

The '343 patent overcomes many of the problems associated with the prior process, which formed a dense precipitate in the compounding solution that was difficult to manage, created a high pH, and generated $Asp^9$-bivalirudin. '343 patent, col.9, 11.3-9. The '343 patent solved the prior problems by efficiently mixing the pH-adjusting solution with the bivalirudin solution to form an amorphous precipitate. Id. at 11.10-17. The amorphous character allows for a more rapid re-dissolution of the precipitate and better control of pH throughout the compounding process. Id. at 11.12-14. As a result, the process described in the '343 patent minimizes $Asp^9$-bivalirudin generation in the compounding solution. See id. at 11.34-35. Yet, even though this method provides a significant manufacturing improvement, a precipitate, albeit amorphous, is nonetheless formed.

A different process for preparing bivalirudin drug product is discussed in CN Publication No. 101244043 ("the '043 publication"). The '043 publication describes a process that involves the steps of (1) dissolving bivalirudin and auxiliary materials in water; (2) adjusting the pH of the solution with a pH conditioner; (3) filtering the solution through 0.22-μm membrane, and (4) freeze-drying the solution to obtain a dried powder. '043 publication, p. 4, ¶2. The '043 publication further discusses dissolving bivalirudin (60-68 mg/mL) in water and adding a solution of sodium carbonate to adjust the pH between 4.5 and 6.5. Id. at p. 4-6. The '043 publication indicates that bivalirudin is "easily soluble in water," and that the dissolved bivalirudin is brought to a pH between 4.5 and 6.5 by addition of a pH conditioner (e.g., sodium carbonate or sodium bicarbonate). Id. at 1. Therefore, given these conditions of bivalirudin solubility, final pH, and type of pH conditioner, the pH of the bivalirudin solution initially should be below the pI of bivalirudin and then pass through the pI to reach the desired pH. Consequently, this process risks the formation of a precipitate.

Taken together, the known processes for preparing a dried bivalirudin drug product should pass through the isoelectric point and result in the formation of a precipitate, which, as described above, can delay production, require human intervention, and cause loss of drug product due to high $Asp^9$-bivalirudin levels. In general, delays in production and human error can heavily impact drug manufacturing costs. Therefore, a method that reduces production delays and minimizes human intervention will enhance product quality and reduce operation costs. In turn, this improvement will better meet the prescriber and patient demands for a dried bivalirudin drug product.

SUMMARY OF THE INVENTION

Applicant has developed a more efficient and cost effective process for preparing a pharmaceutical drug product comprising about 250 mg of bivalirudin that prevents the formation of a bivalirudin precipitate. Applicant has applied this process and variations thereof in the development of a dried bivalirudin drug product and a concentrated liquid bivalirudin drug product.

One aspect of the present invention therefore relates to a method for preventing the formation of a bivalirudin precipitate during the preparation of a pharmaceutical drug product comprising about 250 mg of bivalirudin. The method may comprise (i) preparing an aqueous solution comprising a buffer and a pH greater than the isoelectric point of bivalirudin; (ii) adding bivalirudin salt to the aqueous solution to form a bulk solution; (iii) transferring the bulk solution to one or more vessels; and (iv) drying the bulk solution. In certain embodiments, the aqueous solution comprises a pH greater than the pI of bivalirudin. In additional embodiments, the buffer has a $pK_a$ of about 4 to less than 7. In some embodiments, the pH of the bulk solution is maintained at a level greater than the pI of bivalirudin. In particular embodiments, the bulk solution has a final pH of about 4 to about 7. In additional embodiments, the bulk solution is transferred to provide about 250 mg of bivalirudin to each of the vessels.

In some embodiments of the present invention, the aqueous solution comprises two or more buffers.

In embodiments of the present invention, the aqueous solution has a pH greater than the pI of bivalirudin. In some embodiments, the pH of the aqueous solution is greater than the pI of bivalirudin and less than 10 or is about 5 to about 8. In yet other embodiments, the pH of the aqueous solution is about 6 to about 7.

In various embodiments of the present invention, the buffer has a $pK_a$ of about 4 to less than 7, or about 4.5 to less than 7, or about 4.5 to about 6.5, or about 4 to about 6, or about 4 to about 5. In some embodiments, the buffer has a $pK_a$ of about 4.8.

In embodiments of the present invention, the buffer is acetate, succinate, citrate, benzoate, malate, or propionate.

In certain embodiments of the present invention, the buffer comprises a concentration of about 0.1 M to about 2.0 M, or about 0.1 M to about 1.5 M, or about 0.1 M to about 1.0 M, or about 0.1 M to about 0.5 M. In additional embodiments, the buffer comprises a concentration of about 0.25 M to about 0.5 M.

In some embodiments of the present invention, the bivalirudin salt is added to the aqueous solution in one or more portions to form the bulk solution. In certain embodiments, base is added to the bulk solution after bivalirudin salt is added in one or more portions.

In additional embodiments of the present invention, the bivalirudin salt is solid.

In various embodiments of the present invention, the final pH of the bulk solution is between about 4 and about 7, or between about 4.5 and about 7, or between about 4.5 and about 6.5, or between about 4.5 and about 6, or between about 5 and about 6. In some embodiments, the final pH of the bulk solution is between about 4.5 and about 5.5.

In certain embodiments of the present invention, the method for preparing a pharmaceutical drug product further comprises adding a base to the bulk solution after addition of bivalirudin salt to obtain the final pH of about 4 to about 7, or to obtain the final pH of about 4.5 to about 7, to obtain the final pH of about 4.5 to about 6.5, or to obtain the final pH of about 4.5 to about 6, or to obtain the final pH of about 5 to about 6. In various embodiments, the method further comprises adding a base to the bulk solution after addition of bivalirudin salt to obtain the final pH of about 4.5 to about 5.5.

In particular embodiments, the bulk solution has a final bivalirudin concentration in the range of about 10 mg/mL to about 150 mg/mL, or about 25 mg/mL to about 100 mg/mL, or about 40 mg/mL to about 60 mg/mL. In some embodiments, the bulk solution has a final bivalirudin concentration of about 50 mg/mL.

In various embodiments of the present invention, the method for preparing a pharmaceutical drug product further comprises adding one or more pharmaceutically acceptable excipients to the aqueous solution, to the bulk solution, or to both. In some embodiments, the pharmaceutically acceptable excipient(s) may be added to the bulk solution during the addition of bivalirudin salt, after the addition of bivalirudin salt, or both. In certain embodiments, the pharmaceutically acceptable excipient(s) may be a carrier. In some embodiments, the carrier may be a sugar. In additional embodiments, the sugar may be mannitol.

In certain embodiments of the present invention, the method for preparing a pharmaceutical drug product further comprises transferring the bulk solution into one or more vessels. In additional embodiments, a volume of the bulk solution is transferred to provide about 250 mg of bivalirudin to each of the vessels.

In various embodiments of the present invention, the method for preparing a pharmaceutical drug product further comprises sterilizing the bulk solution before drying the bulk solution. In some embodiments, sterilizing the bulk solution is by aseptic filtration.

In certain embodiments of the present invention, drying the bulk solution is by lyophilization. In additional embodiments, drying the bulk solution is by spray-drying.

Another aspect of the present invention relates to a dried bivalirudin drug product that is administered to a patient in need thereof. In some embodiments, the dried bivalirudin drug product comprises bivalirudin, buffer components, and a pharmaceutically acceptable carrier. In certain embodiments, buffer components are components that result from the removal of water from a buffer. In embodiments of the present invention, the buffer components are components resulting from the removal of water from acetate, succinate, citrate, benzoate, malate, or propionate buffers.

In certain embodiments, the pharmaceutically acceptable excipient(s) in the dried bivalirudin drug product may be a carrier. In some embodiments, the carrier may be a sugar. In additional embodiments, the sugar may be mannitol.

In certain embodiments, the dried bivalirudin drug product is prepared by the method of preparing a pharmaceutical drug product of the invention.

Yet another aspect of the present invention relates to a concentrated liquid bivalirudin drug product that is administered to a patient in need thereof. In various embodiments of the present invention, the concentrated liquid bivalirudin drug product comprises bivalirudin, a buffer, and a pharmaceutically acceptable carrier.

In some embodiments of the concentrated liquid bivalirudin drug product, the buffer is acetate, succinate, citrate, benzoate, malate, or propionate.

In certain embodiments, the pharmaceutically acceptable excipient(s) in the concentrated liquid bivalirudin drug product may be a carrier. In some embodiments, the carrier may be a sugar. In additional embodiments, the sugar may be mannitol.

In additional embodiments, the concentrated liquid bivalirudin drug product is prepared by a method comprising (i) preparing an aqueous solution comprising a buffer; (ii) adding bivalirudin salt to the aqueous solution to form a bulk solution and (iii) transferring the bulk solution to one or more vessels, according to the present invention. In various embodiments, the method further comprises sterilizing the bulk solution.

These and other embodiments are disclosed or are obvious from and encompassed by, the following Detailed Description.

DETAILED DESCRIPTION

The present invention generally is directed towards a method for preventing the formation of a bivalirudin precipitate during the preparation of a pharmaceutical drug product comprising about 250 mg of bivalirudin. The present invention is also directed towards a dried bivalirudin drug product and a concentrated liquid bivalirudin drug product that are administered to a patient in need thereof.

DEFINITIONS

As used herein, the term "bivalirudin" refers to a drug substance in the free base form. Bivalirudin has a molecular weight of 2180 daltons (anhydrous). The amino acid sequence of bivalirudin is: (D-Phe)-Pro-Arg-Pro-Gly-Gly-Gly-Gly-Asn-Gly-Asp-Phe-Glu-Glu-Ile-Pro-Glu-Glu-Tyr-Leu (SEQ ID NO: 1). The chemical name of bivalirudin is D-Phenylalanyl-L-Prolyl-L-Arginyl-L-Prolyl-Glycyl-Glycyl-Glycyl-Glycyl-L-Asparagyl-Glycyl-L-Aspartyl-L-Phenylalanyl-L-Glutamyl-L-Glutamyl-L-Isoleucyl-L-Prolyl-L-Glutamyl-L-Glutamyl-L-Tyrosyl-L-Leucine.

As used herein, the term "bivalirudin salt" refers to a drug substance that is a salt of bivalirudin. For example, bivalirudin may be a trifluoroacetate salt (D-Phenylalanyl-L-Prolyl-L-Arginyl-L-Prolyl-Glycyl-Glycyl-Glycyl-Glycyl-L-Asparagyl-Glycyl-L-Aspartyl-L-Phenylalanyl-L-Glutamyl-L-Glutamyl-L-Isoleucyl-L-Prolyl-L-Glutamyl-L-Glutamyl-L-Tyrosyl-L-Leucine trifluoroacetate salt). The bivalirudin salt used herein has a pH in water that is less than the pI of bivalirudin.

Methods for the synthesis of bivalirudin and/or bivalirudin salt may include, but are not limited to, solid-phase peptide synthesis, solution-phase peptide synthesis, or a combination of solid-phase and solution-phase procedures (e.g., U.S. Pat. No. 5,196,404; Okayama et al., *Chem. Pharm. Bull.* 1996, 44: 1344-1350; Steinmetzer et al., *Eur. J. Biochem.* 1999, 265: 598-605; PCT Publication No. WO 91/02750; and U.S. Publication No. 20070093423).

Bivalirudin undergoes degradation by pathways that are common to other peptides, including D-Phe-Pro cleavage (resulting in [3-20]-bivalirudin), deamidation, hydrolysis, and isomerization.

Bivalirudin is susceptible to deamidation via the $Asn^9$-$Gly^{10}$ residues that can form [9-10]-cycloimido bivalirudin, wherein $Asn^9$ and $Gly^{10}$ form a succinimide. This [9-10]-cycloimido bivalirudin can remain as an impurity or can undergo hydrolysis to form $Asp^9$-bivalirudin (SEQ ID NO: 2), iso$Asp^9$-bivalirudin or isomers thereof. $Asp^9$-bivalirudin is a known degradation (see U.S. Publication No. 20070093423) and process impurity (see U.S. Pat. Nos. 7,598,343 and 7,582,727; application Ser. No. 12/180,550).

Bivalirudin is also susceptible to isomerization at the L-phenylalanine residue at position 12 to give the D-isomer of bivalirudin, creating the impurity D-$Phe^{12}$-bivalirudin.

As used herein, the term "buffer" is a solution that resists changes in pH and is composed of one or more ionic compounds. An example of a buffer is a mixture of a weak acid and its conjugate base. Buffers can be characterized by their $K_a$ values. The $K_a$ value is used to describe the tendency of ionic compounds to dissociate and is called the acid dissociation constant.

As used herein, the term "$pK_a$" refers to a value that is defined from $K_a$ and can be calculated from the equation: $pK_a = -Log_{10}K_a$. The pH range for a buffer that optimally resists changes in pH is commonly referred to as the buffering capacity, and is generally ±one pH unit from the $pK_a$ of the buffer.

As used herein, the term "pH" is a measure of hydrogen-ion concentration, as commonly used in the art. The pH provides a measure on a scale from 0 to 14 of the acidity or alkalinity of a solution. Blood is essentially neutral at a pH of 7.4. To prevent stinging, burning, pain, irritation or tissue damage during administration, a parenteral solution may have a pH close to that of blood.

As used herein, the term "isoelectric point" or "pI" refers to the pH at which a molecule, such as bivalirudin, carries no net charge. The pI of bivalirudin is about 3.6.

As used herein, the term "precipitate" refers to a material that is formed from a solution.

As used herein, the term "buffer components" refers to the components of the buffer that are added to water to create the buffer and that remain after the buffer is dried, e.g., water is removed from the buffer. For example, if acetate buffer is formed from mixing acetic acid and sodium acetate, the buffer components are acetic acid and sodium acetate.

As used herein, the term "sterilizing" refers to the elimination of essentially all forms of microbial life by an appreciable amount to meet the criteria outlined in the U.S. Pharmacopeia. See U.S. Pharmacopeia 32, NF 27, 1 (2009) 80-86.

As used herein, the term "drying" refers to a method of removing solvents or volatile components from a solution.

As used herein, the term "base" refers to an inorganic base or an organic base, as commonly known in the art. The base may include, but is not limited to, alkaline carbonate, alkaline bicarbonate, alkaline earth metal carbonate, alkaline hydroxide, alkaline earth metal hydroxide and amine. For example, the base may be lithium hydroxide, potassium hydroxide, cesium hydroxide, sodium hydroxide, calcium carbonate, sodium carbonate, sodium bicarbonate, sodium acetate, or the like.

As used herein, the term "acid" refers to an inorganic mineral acid such as hydrochloric, hydrobromic, sulfuric, phosphoric, nitric, and the like; or an organic acid such as acetic, succinic, tartaric, ascorbic, citric, glutamic, benzoic, methanesulfonic, ethanesulfonic, trifluoroacetic or the like.

As used herein, the term "osmolarity" refers to the concentration (osmoles, Osm) of the dissolved substances (solute) per liter of solution (Osm/L) that contributes to a solution's osmotic pressure. The osmolarity of plasma has a range of about 275-295 mOsm/L. As used herein, the term "osmolality" refers to the concentration of the dissolved substances per kilogram of solvent and is considered representative of osmolarity.

As used herein, the term "concentrated liquid bivalirudin" refers to a pharmaceutical drug product comprising bivalirudin at a concentration of about 50 mg/mL. The concentrated liquid bivalirudin can be diluted before administration to a patient.

Method for Preparing a Pharmaceutical Drug Product Comprising about 250 Mg of Bivalirudin The present invention relates to a method for preventing the formation of a bivalirudin precipitate during the preparation of a pharmaceutical drug product comprising 250 mg bivalirudin. The method may comprise (i) preparing an aqueous solution comprising a buffer and a pH greater than the isoelectric point of bivalirudin; (ii) adding bivalirudin salt to the aqueous solution to form a bulk solution; (iii) transferring the bulk solution to one or more vessels; and (iv) drying the bulk solution.

It is essential that the aqueous and bulk solutions in each step of the present invention avoid passing through the pI of bivalirudin. As described above, previous methods of preparing bivalirudin drug product featured an initial step of obtaining a solution comprising bivalirudin ("bivalirudin solution") having a pH below the pI. In order to arrive at a bivalirudin drug product having a pH appropriate for parenteral administration, the pH of the bivalirudin solution increased, passing through the pI of bivalirudin. As a result, a bivalirudin precipitate formed, which caused various manufacturing challenges. Moreover, in some instances, the presence of the precipitate along with the exposure to high alkaline pH during the process generated Asp$^9$-bivalirudin.

In contrast, the present invention not only avoids passing through the pI of bivalirudin during the process and prevents the formation of a precipitate, but also controls the generation of Asp$^9$-bivalirudin. In the method of the present invention, there are several embodiments that may be considered including the pK$_a$ of the buffer, the pH of the aqueous solution, the concentration of the buffer, the method of adding bivalirudin salt, the pH of the bulk solution during the addition process, the optional addition of a base during or after the addition of bivalirudin salt, the final pH of the bulk solution, the final concentration of bivalirudin in the bulk solution, the optional addition of a pharmaceutically acceptable excipient, the osmolality of the final bulk solution, and the method of drying the bulk solution.

1) Preparing an Aqueous Solution Comprising a Buffer

As described above, the method of the present invention may involve the preparation of an aqueous solution comprising a buffer. Various buffers may be used in the present invention, such as buffers having a pK$_a$ greater than the pI of bivalirudin. Some examples of buffers and their corresponding pK$_a$ include, but are not limited to, those shown in Table 1.

TABLE 1

Buffers and Corresponding pK$_a$ at 25° C.

| Buffer | pK$_a$ |
|---|---|
| Maleate | 2.0 (pK$_1$) |
| Glycine | 2.4 |
| Malate | 3.4 (pK$_1$) |
| Formate | 3.8 |
| Benzoate | 4.2 |
| Succinate | 4.2 (pK$_1$) |
| Citrate | 4.8 (pK$_2$) |
| Acetate | 4.8 |
| Propionate | 4.9 |
| Malate | 5.1 (pK$_2$) |
| Succinate | 5.6 (pK$_2$) |
| Histidine | 6.0 |
| 2-(N-Morpholino)ethanesulfonic acid (MES) | 6.1 |
| Cacodylate | 6.3 |
| Maleate | 6.2 (pK$_2$) |
| Citrate | 6.4 (pK$_3$) |
| Carbonate | 6.4 (pK$_1$) |
| 2-[Bis(2-hydroxyethyl)amino]-2-(hydroxymethyl)propane-1,3-diol (BIS-TRIS) | 6.5 |
| N-(2-Acetamido)iminodiacetic Acid (ADA) | 6.6 |
| 1,3-Bis(tris(hydroxymethyl)methylamino) propane (BIS-TRIS propane) | 6.8 (pK$_1$) |
| Piperazine-1,4-bis(2-ethanesulfonic acid) (PIPES) | 6.8 |
| N-(2-Acetamido)-2-aminoethanesulfonic acid (ACES) | 6.8 |
| 3-(N-Morpholino)-propanesulfonic acid (MOPSO) | 6.9 |
| Imidazole | 7.0 |
| Phosphate | 7.2 |
| Tris(hydroxymethyl)aminomethane (TRIS) | 8.1 |

See Sigma Aldrich Website and Gordon, A J and Ford, R A, *The Chemist's Companion: A Handbook of Practical Data, Techniques, and References*, John Wiley & Sons, New York, 1972 for pK$_a$ values.

In certain embodiments, the buffer has a pK$_a$ of about 4 to less than 7, or about 4.5 to less than 7, or about 4.5 to about 6.5. In other embodiments, the buffer has a pK$_a$ of about 4 to about 6. In yet other embodiments, the buffer has a pK$_a$ of about 4 to about 5.

The present invention also encompasses an aqueous solution comprising a combination of two or more buffers. Preferably, one of the buffers in the combination has a pK$_a$ above the pI of bivalirudin, for example, a pK$_a$ of about 4 to less than 7, or about 4 to about 6.5, or about 4 to about 6, or about 4 to about 5. Examples of buffer combinations include, but are not limited to BIS-TRIS/acetate, and malate/citrate. In certain embodiments, pre-mixed buffers may be used.

The buffers of the present invention may be prepared by different methods, as known in the art. For instance, in certain embodiments, a buffer comprising two or more components (e.g., a weak acid and a weak base, or two weak bases) may be prepared by adding these components to water and adjusting the pH by addition of an acid or base. As an example, an acetate buffer may be prepared by adding acetic acid and sodium acetate to water, and then adjusting the pH of the resulting solution by the addition of an acid or base. In other embodiments, a buffer comprising two or more components may be prepared by mixing a specific amount of a first component in solution with a specific amount of a second component in solution to obtain a desired pH. For example, an acetate buffer may be prepared by mixing a specific amount of sodium acetate with a specific amount of acetic acid to obtain a buffer with a desired pH. Other methods of preparing a buffer are known in the art.

The base used to adjust the pH of the buffer may be an organic base or an inorganic base, as described above. The base may be added neat or dissolved in a solvent. Solvents may include aqueous and non-aqueous liquids, or mixtures thereof, including but not limited to, water and alcohols, as known in the art.

Certain embodiments of the present invention are directed to a method of preparing an aqueous solution comprising a buffer and a pH within about one unit of the buffer's $pK_a$ to achieve the buffer's optimal buffering capacity. Examples of aqueous solutions include, but are not limited to, those comprising a pH of 5.2 and buffers having a $pK_a$ of about 4.2; or a pH of about 5.6 and buffers having a $pK_a$ of 4.8. In other embodiments, the aqueous solution may comprise a pH and buffer, wherein the pH is higher than the optimal buffering capacity of the buffer, for example, a pH of about 8.0 and buffers having a $pK_a$ of 4.8.

The pH of the aqueous solution may be greater than the pI of bivalirudin. Examples of such aqueous solutions include, but are not limited to, aqueous solutions having a pH greater than the pI of bivalirudin and less than 10, aqueous solutions having a pH of about 5 to about 8, and aqueous solutions having a pH of about 6 to about 7.

Buffer concentrations of the present invention may comprise ranges that include, but are not limited to, about 0.1 M to about 2.0 M, or about 0.1 M to about 1.5 M, or about 0.1 M to about 1.0 M, or about 0.1 M to about 0.5 M. In additional embodiments, the buffer comprises a concentration of about 0.25 M to about 0.5 M. The optimal buffer concentration may depend, for example, on the $pK_a$ of the buffer, the pH of the aqueous solution, the desired pH of the bulk solution, and the concentration of bivalirudin.

2) Adding Bivalirudin Salt to the Aqueous Solution to Form a Bulk Solution

Bivalirudin salt is added to the aqueous solution, which comprises a buffer, to form a bulk solution. The bulk solution can refer to the solution that is formed during or after the addition of the bivalirudin salt to the aqueous solution. Bivalirudin salt may be added to the aqueous solution using various methods. For example, bivalirudin salt may be added as a solid or as a solution (e.g., dissolved in water).

Bivalirudin salt may be added to the aqueous solution continuously, or intermittently in two or more portions. The two or more portions may be equal amounts, unequal amounts, or a combination thereof. The period of time between the addition of each portion may also vary. In some embodiments, a subsequent portion of bivalirudin salt is added after the preceding portion of bivalirudin salt has significantly dissolved. In certain embodiments, bivalirudin salt is added in three or more, or five or more, or ten or more portions.

During the addition of bivalirudin salt, the pH of the resulting bulk solution may be maintained above the pI of bivalirudin. In some embodiments, during the addition of bivalirudin salt, the pH of the resulting bulk solution may be maintained above 4.4, or the pH of the resulting bulk solution may be maintained above 4.7.

In other embodiments, base may be added to the bulk solution during or after the addition of bivalirudin salt to maintain the pH of the bulk solution above the pI of bivalirudin. Base may be added to the bulk solution between portions of bivalirudin salt. The base added to the bulk solution may be an organic base or an inorganic base, as described above. The base may be added neat or dissolved in a solvent. Solvents may include aqueous and non-aqueous liquids, or mixtures thereof, including but not limited to, water and alcohols, as known in the art.

The final pH of the bulk solution will be approximately the pH of bivalirudin drug product administered parenterally to patients in need thereof. Therefore, the pH of the bulk solution should be compatible with such administration (e.g., the pH of blood is about 7.4) while within a range that does not promote the generation of $Asp^9$-bivalirudin. In certain embodiments, the ranges for the final pH of the bulk solution may include, but are not limited to, between about 4 and about 7, between about 4.5 and about 7, between about 4.5 and about 6.5, between about 4.5 and about 6, between about 4.5 and about 5.5, and between about 5 and about 6.

The final pH of the bulk solution may be adjusted to a desired pH, for instance by addition of an acid or base. As such, in some embodiments, the final pH may be adjusted to about 4 or above, or between about 4 and about 7, or between about 4.5 and about 7, or between about 5 and about 6. The base used to adjust the final pH may be an organic base or an inorganic base, as described above. The base may be added neat or dissolved in a solvent. Solvents may include aqueous and non-aqueous liquids, or mixtures thereof, including but not limited to, water and alcohols, as known in the art. The acid used to adjust the final pH may be, for example, one or more inorganic mineral acids or organic acids, as described above.

The osmotic pressure of the bulk solution may also be considered in the present invention. In certain embodiments, the osmolality of the bulk solution may be less than about 3000 mOsm/kg. In other embodiments, the bulk solution may have an osmolality of less than about 2000 mOsm/kg. In still other embodiments, the bulk solution may have an osmolality of less than about 1000 mOsm/kg.

The bulk solution may have a final bivalirudin concentration in the range of about 10 mg/mL to about 150 mg/mL, or about 25 mg/mL to about 100 mg/mL, or about 40 mg/mL to about 60 mg/mL. In certain embodiments, the bulk solution may have a final bivalirudin concentration of about 50 mg/mL. The final bivalirudin concentration may dictate the buffer concentration in the aqueous solution. For example, a higher final bivalirudin concentration (e.g., about 150 mg/mL) may require a higher concentration of buffer in order to maintain the pH of the bulk solution above the pI of bivalirudin. The final bivalirudin concentration may also influence the final pH of the bulk solution. For instance, a lower final bivalirudin concentration (e.g., about 10 mg/mL) may be dissolved at a pH close to the pI of bivalirudin (e.g., about 4).

One or more pharmaceutically acceptable excipients may be added to the aqueous solution, to the bulk solution, or to both. For example, the pharmaceutically acceptable excipient(s) may be added to the bulk solution during the addition of bivalirudin salt, after the addition of bivalirudin salt, or both. In some embodiments, the pharmaceutically acceptable excipient may be a sugar, such as mannitol. In certain embodiments, the final concentration of mannitol is about 10 mg/mL to about 40 mg/mL, or about 20 mg/mL to about 30 mg/mL, or about 25 mg/mL.

The bulk solution may be sterilized, for example, by a thermal process at elevated temperatures or a non-thermal process such as filtration through bacteria-retaining filters. Subsequently, all operations should be carried out in an aseptic manner so that contamination will not be introduced into the filtrate. See Alfonso Gennaro, ed. *Remington: The Science*

*and Practice of Pharmacy* 801 (20th ed. 2000). In certain embodiments, the bulk solution may be filtered through a 0.22 µm sterilized filter.

3) Transferring the Bulk Solution

The method of the present invention may further comprise transferring the bulk solution into one or more vessels. The step of transferring may be automated (e.g., by machines which distribute the bulk solution into the one or more vessels) or manual (e.g., by hand-held pipettes or by pouring). The vessels used in this invention may include any means that can hold a volume of liquid as known in the art, such as vials or containers. The desired amount of bivalirudin in each vessel may be about 250 mg.

The volume of bulk solution that may be transferred to vessels can depend on the concentration of bivalirudin in the bulk solution. For example, if the concentration of bivalirudin in the bulk solution is 50 mg/mL and the desired amount of bivalirudin in each vessel is about 250 mg, then 5 mL of bulk solution will be transferred to each vessel. On the other hand, if the concentration of bivalirudin in the bulk solution is about 100 mg/mL and the desired amount of bivalirudin in each vessel is about 250 mg, then 2.5 mL of bulk solution will be transferred to each vessel.

By the steps detailed herein, the method of the present invention avoids the formation of a bivalirudin precipitate, as well as controls the generation of $Asp^9$-bivalirudin during the preparation of the bulk solution. As described above, $Asp^9$-bivalirudin can be generated as a process impurity. It is an important characteristic of the method of the present invention that $Asp^9$-bivalirudin generation is controlled during the preparation of the bulk solution. In various embodiments, no appreciable amount of $Asp^9$-bivalirudin generation was detected in the bulk solution.

4) Drying the Bulk Solution

The method of the present invention may comprise drying the bulk solution. The drying method is not limited to any particular method, and may be a drying method that is usually used in drying pharmaceutical drug products. The method typically includes vacuum-drying, evaporative-drying, freeze-drying, spontaneous drying, spray-drying or a combination thereof.

Suitable in this regard is spray-drying, or drying using Duprat® drums, or alternatively freeze-drying (lyophilization). Freeze-drying is a preferred method for drying since biologicals and pharmaceuticals that are relatively unstable in an aqueous solution can be dried without elevated temperatures (thereby eliminating the adverse thermal effects), and then stored in a dry state where there are few stability problems. See Alfonso Gennaro, ed. *Remington: The Science and Practice of Pharmacy* 802 (20th ed. 2000).

Dried Bivalirudin Drug Product

Another aspect of the present invention relate to a dried pharmaceutical drug product comprising bivalirudin, buffer components, and a pharmaceutically acceptable excipient. The dried bivalirudin drug product may be a solid such as a powder, cake, or combination thereof. Certain embodiments of the dried bivalirudin drug product of the present invention may contain various impurities, which include, but are not limited to, $Asp^9$-bivalirudin. The levels of these impurities generally reflect the amount of impurities present in the drug substance used to prepare the dried bivalirudin drug product.

The buffer components of the dried drug product include the components that comprise the buffer that was used in the process of preparing the drug product. For example, a dried bivalirudin drug product may comprise acetic acid and sodium acetate components.

A dried bivalirudin drug product may comprise one or more pharmaceutically acceptable excipients. For example, the pharmaceutically acceptable excipient(s) may be a sugar, such as mannitol.

The dried pharmaceutical bivalirudin drug product may be generated by the method of the present invention.

Concentrated Liquid Pharmaceutical Drug Product

Another aspect of the present invention is a concentrated liquid bivalirudin drug product. As described above, applicant has developed a more efficient and cost effective method for the preparation of a bivalirudin drug product that avoids the formation of a bivalirudin precipitate. This method may also be applied to the manufacture of a concentrated liquid bivalirudin drug product, which does not require reconstitution prior to administering to a patient. A concentrated liquid bivalirudin drug product may be generated by a method comprising steps (i), (ii), and (iii) of the present invention. The method for generating the concentrated liquid bivalirudin drug product may include a sterilization step as described above. Currently, there is no FDA-approved dosage form of bivalirudin other than Angiomax®, a lyophilized powder. Certain embodiments of the present invention relate to a concentrated liquid bivalirudin drug product comprising bivalirudin and a buffer. The buffer may have a $pK_a$ of about 4 to less than 7, or about 4 to about 6.5, or about 4 to about 6, or about 4 to about 5 (see e.g., Table 1). In additional embodiments, the concentrated liquid bivalirudin drug product may include one or more buffers. The buffer concentrations may comprise ranges that include, but are not limited to, from about 0.1 M to about 2 M, and from about 0.25 M to 0.5 M.

In some embodiments, the concentrated liquid bivalirudin drug product has a final pH in the range of between about 4 and about 7, between about 4.5 and about 7, between about 4.5 and about 6.5, between about 4.5 and about 6, between about 4.5 and about 5.5, and between about 5 and about 6.

Certain embodiments of the concentrated liquid bivalirudin drug product of the present invention may contain various impurities, which include, but are not limited to, $Asp^9$-bivalirudin. The levels of these impurities generally reflect the amount of impurities present in the drug substance used to prepare the concentrated liquid bivalirudin drug product.

Further, a concentrated liquid bivalirudin product of the present invention may relate to one or more of the characteristics described above.

The invention will now be further described by way of the following non-limiting examples, which further illustrate the invention; such examples are not intended, nor should they be interpreted, to limit the scope of the invention.

EXAMPLES

The solid bivalirudin salt used in these examples contains approximately 8-12% trifluoroacetic acid. For example, an amount of 2.81 g of bivalirudin trifluoroacetic acid salt equates to approximately 2.5 g of bivalirudin.

Example 1

Four different buffers were used to prepare aqueous solutions, each having a pH of 5.25, to determine whether the addition of bivalirudin salt to these aqueous solutions would result in changes in pH or the formation of a precipitate. These buffers, having varying $pK_a$ values, include acetate ($pK_a$ 4.8), succinate ($pK_a$ 4.2, 5.6), citrate ($pK_a$ 4.8, 6.0, 6.4), and phosphate ($pK_a$ 7.2).

A. Acetate Buffer

To prepare an aqueous solution comprising an acetate buffer (0.1 M), dilute acetic acid (0.02 M, 0.0608 g) was added to sterile water for injection ("WFI"; 40 mL), and sodium acetate trihydrate (0.5412 g) was added with stirring. The resulting pH was adjusted to 5.26 using sodium hydroxide (0.1 N, 0.1 g). Solid bivalirudin salt (2.8105 g) was slowly added while stirring to form a bulk solution. Observations recorded during the addition of bivalirudin salt to the aqueous solution are shown in Table 2.

B. Citrate Buffer

To prepare an aqueous solution comprising a citrate buffer (0.1 M), citric acid monohydrate (1.0501 g) was added to sterile WFI (40 mL) and sodium hydroxide (1 N, 12.2 g) was added while stirring to obtain a pH of 5.25. Solid bivalirudin salt (2.8135 g) was slowly added with stirring to form a bulk solution. Observations recorded during the addition of bivalirudin salt to the aqueous solution are shown in Table 2.

C. Succinate Buffer

To prepare an aqueous solution comprising a succinate buffer (0.1 M), succinic acid (0.5901 g) was added to sterile WFI (40 mL) and sodium hydroxide (1 N, 9 mL) was added while stirring to obtain a pH of 5.25. Solid bivalirudin salt (2.8113 g) was slowly added with stirring to form a bulk solution. Observations recorded during the addition of bivalirudin salt to the aqueous solution are shown in Table 2.

D. Phosphate Buffer

To prepare an aqueous solution comprising a phosphate buffer (0.1 M), sodium dihydrogen phosphate dihydrate (0.7817 g) was added to sterile WFI (40 mL) and sodium hydroxide (1 N, 0.28 g) was added while stirring to obtain a pH of 5.26. Solid bivalirudin salt (2.8128 g) was slowly added with stirring to form a bulk solution. Observations recorded during the addition of bivalirudin salt to the aqueous solution are shown in Table 2.

TABLE 2

Observations During the Addition of Solid Bivalirudin Salt to Aqueous Solutions Comprising Various Buffers and Having a pH of about 5.25.

| Buffer (pK$_a$) | Final pH | Change in pH | Observation |
| --- | --- | --- | --- |
| Acetate (4.8) | 4.10 | 1.16 | Particles of bivalirudin salt did not dissolve even after about 5 hours of mixing. |
| Citrate (4.8, 6.0, 6.4) | 4.39 | 0.86 | Same as above. |
| Succinate (4.2, 5.6) | 4.33 | 0.92 | Same as above. |
| Phosphate (7.2) | 2.84 | 2.42 | Bivalirudin salt dissolved in about 15 minutes, but the pH dropped below the pI of bivalirudin. |

Due to the insolubility of bivalirudin salt (in aqueous solutions comprising acetate, citrate, or succinate buffers) or passage of the pH through the pI (in aqueous solutions comprising phosphate buffer), addition of water to achieve a final bivalirudin concentration of about 50 mg/mL was not performed, resulting in a final bivalirudin concentration greater than about 50 mg/mL. The pH of each bulk solution decreased as bivalirudin salt was added, although the final pH of the bulk solution containing phosphate resulted in the lowest final pH. These results suggest that the final pH of the bulk solution and the concentration of bivalirudin may be important in ensuring that bivalirudin salt is completely dissolved.

Example 2

Aqueous solutions comprising citrate buffer at concentrations of 0.25 M and 0.5 M were prepared to determine whether a citrate buffer can be used to prevent formation of a bivalirudin precipitate and to maintain a pH greater than the pI of bivalirudin.

To prepare the aqueous solution comprising 0.25 M citrate buffer, citric acid monohydrate (0.7989 g) was added to sterile WFI (40 mL), and trisodium citrate (2.2534 g) was added. Sodium hydroxide (1 N, 4.5 mL) was added to adjust the pH to 5.25. Solid bivalirudin salt (2.81 g) was slowly added and stirred until the bivalirudin salt dissolved (about 15 minutes) to form a bulk solution having a pH of 4.67. The final pH was adjusted to 5.23 with the addition of sodium hydroxide (1 N, 4.7 mL).

To prepare the aqueous solution comprising 0.5 M citrate buffer, citric acid monohydrate (1.5969 g) was added to sterile WFI (40 mL), and trisodium citrate (4.4904 g) was added. Sodium hydroxide (1 N, 9.0 mL) was added to adjust the pH to 5.24. Solid bivalirudin salt (2.81 g) was slowly added and stirred until the bivalirudin salt dissolved (about 15 minutes) to form a bulk solution having a pH of 5.07. The osmolality of the bulk solution was 1093 mOsm/kg. A portion of the bulk solution (5 mL) was diluted to 50 mL using 0.9% sodium chloride solution for injection and the resulting osmolality was 343 mOsm/kg. No bivalirudin precipitate was observed during the formation of either bulk solution. A final concentration of about 50 mg/mL bivalirudin was not obtained in either bulk solution since, in both cases, the bulk solution volume after the final pH adjustment exceeded the volume required to produce the desired concentration. These results demonstrate that solid bivalirudin salt was completely dissolved at a final pH of 4.67 and 5.07, indicating that aqueous solutions comprising citrate buffers can be used to prepare a bulk solution that maintains a pH above the pI of bivalirudin and avoids the formation of a precipitate.

Example 3

Concentrated liquid bivalirudin drug product and dried bivalirudin drug product were prepared using an acetate buffer (0.5 M), citrate buffer (0.5 M) or succinate buffer (0.5 M) to determine whether aqueous solutions having a starting pH of about 5.3 that are prepared from these buffers can prevent the formation of a bivalirudin precipitate, allow the solid bivalirudin salt to dissolve, and control the generation of impurities during the method for preparing the bivalirudin drug product.

A. Acetate Buffer

An aqueous solution comprising acetate buffer was prepared by adding 0.2779 g of acetic acid to 38 mL of sterile WFI, followed by the addition of 2.7834 g of sodium acetate trihydrate. The resulting pH was 5.28. Solid bivalirudin salt (2.8118 g) was slowly added and stirred until the bivalirudin salt dissolved (about 20 minutes) to form a bulk solution having a pH of 4.85. No bivalirudin precipitate was observed during the formation of the bulk solution. The pH was adjusted to 5.23 by the addition of sodium hydroxide (1 N, 4.2 g) and q.s. with sterile WFI to a final volume of 50 mL. The final bivalirudin concentration of the bulk solution was about 50 mg/mL, and the osmolality was about 1063 mOsm/kg.

B. Citrate Buffer

An aqueous solution comprising citrate buffer was prepared by adding 0.5255 g of citric acid monohydrate to 35 mL of sterile WFI, followed by the addition of 5.8145 g of trisodium citrate anhydrous. Hydrochloric acid (1 N, 0.8 mL) was added to adjust the pH to 5.27. Solid bivalirudin salt (2.81 g) was slowly added and stirred until the bivalirudin salt dissolved (about 15 minutes) to form a bulk solution having a pH of 4.92. No bivalirudin precipitate was observed during the formation of the bulk solution. Sodium hydroxide (1 N, 6.83 mL) was then added to adjust the pH to 5.24 and q.s. with sterile WFI to a final volume of 50 mL. The final bivalirudin concentration of the bulk solution was about 50 mg/mL.

C. Succinate Buffer

An aqueous solution comprising succinate buffer was prepared by adding 0.8928 g of succinic acid to 35 mL of sterile WFI, followed by the addition of 2.8410 g of disodium succinate. Sodium hydroxide (1 N, 1 mL) was added to adjust the pH to 5.20. Solid bivalirudin salt (2.81 g) was slowly added and stirred until the bivalirudin salt dissolved (about 35 minutes) with stirring to form a bulk solution having a pH of 5.02. No bivalirudin precipitate was observed during the formation of the bulk solution. Sodium hydroxide (1 N, 5.82 mL) was then added to adjust the pH to 5.25 and q.s. with sterile WFI to a final volume of about 50 mL. The final bivalirudin concentration of the bulk solution was about 50 mg/mL.

D. HPLC Conditions

HPLC conditions for the analysis of the liquid concentrate and lyophilized drug products are shown in Table 3.

TABLE 3

HPLC Conditions for Analysis of Bivalirudin Drug Product.

| | HPLC Conditions |
|---|---|
| Instrument | Agilent 1200 Series |
| Column | Vydac C18, 5 μm, 250 mm × 4.6 mm |
| Column temperature | 40° C. |
| Detector | UV at 215 nm |
| Pump Mode | Gradient |
| Flow Rate | 1.2 mL/min |
| Injection volume | 40 μL |
| Run time | 40 minutes |
| Column Loading | Both a low and a high (50-fold) concentration of drug product were used to determine % AUC of impurities |
| Mobile Phase A | 0.05 M Sodium Acetate Buffer (pH 6.5) |
| Mobile Phase B | 0.05 M Sodium Acetate/50 % Acetonitrile |

The gradient program is shown in Table 4.

TABLE 4

HPLC Gradient Program.

| Time | % Mobile Phase B |
|---|---|
| 0 | 10 |
| 5 | 15 |
| 30 | 35 |
| 35 | 35 |
| 35.01 | 10 |
| 40 | 10 |

E. Purity Determinations

Each of the bulk solutions described above (3A-3C) was sterile filtered (0.22-μm Durapore Membrane) and divided into 5 mL portions that were transferred into glass vials and stoppered. Two vials were stored as a liquid concentrate at ambient temperature, while the remaining vials were stored at −20° C. and then dried by lyophilization. Purity determinations for the liquid concentrate and lyophilized drug products at t=0 are presented in Tables 5 and 6, where the values are measurements from a single vial.

TABLE 5

Determination of Bivalirudin Purity in a Liquid Concentrate and a Lyophilized Drug Product.

| Buffer (pK$_a$) | Drop in pH[1] | Dosage Form | Change in Asp$^9$ (%)[2] | Final Asp$^9$ (%) | Total Impurity (%) |
|---|---|---|---|---|---|
| Acetate (4.8) | 0.5 | Concentrate | 0 | 0.40 | 1.4 |
| | | Lyophilized | 0 | 0.41 | 1.2 |
| Citrate (4.8, 6.0, 6.4) | 0.4 | Concentrate | 0 | 0.42 | 1.4 |
| | | Lyophilized | 0 | 0.41 | 1.1 |
| Succinate (4.2, 5.6) | 0.3 | Concentrate | 0 | 0.41 | 1.4 |
| | | Lyophilized | 0 | 0.41 | 1.2 |

[1] The drop in pH indicates the change in pH from the initial pH of the aqueous solution (before addition of the bivalirudin salt) to the pH resulting after bivalirudin salt addition (before any pH adjustment).
[2] The change in Asp$^9$-bivalirudin refers to the difference in Asp$^9$-bivalirudin between the drug substance and the final drug product (t = 0). As such, the change in Asp$^9$-bivalirudin measured in the liquid concentrate or lyophilized drug products is representative of Asp$^9$-bivalirudin generated during the formation of the bulk solution.

TABLE 6

Determination of Bivalirudin Purity in a Liquid Concentrate and a Lyophilized Drug Product.

| Buffer (pK$_a$) | Dosage Form | [9-10]-cyclo (%)[1] | [1-11]-Bvl (%) | [12-20]-Bvl (%) | [3-20]-Bvl (%) | [11-12]-cyclo (%) |
|---|---|---|---|---|---|---|
| Acetate (4.8) | Concentrate | 0.12 | 0.17 | 0.29 | 0.23 | 0.14 |
| | Lyophilized | 0.09 | 0.16 | 0.28 | 0.18 | 0.07 |
| Citrate (4.8, 6.0, 6.4) | Concentrate | 0.29 | 0.17 | 0.28 | 0.24 | 0.11 |
| | Lyophilized | 0.12 | 0.18 | 0.27 | 0.16 | 0.08 |
| Succinate (4.2, 5.6) | Concentrate | 0.26 | 0.17 | 0.26 | 0.31 | 0.12 |
| | Lyophilized | 0.11 | 0.17 | 0.27 | 0.21 | 0.07 |

[1] Contains minor co-eluting D-Phe$^{12}$ impurity.

The results suggest that buffers having a pK$_a$ ranging from 4.2 to 6.4 are well suited to (a) maintain the pH of bulk solutions (containing about 50 mg/mL of bivalirudin) above the pI of bivalirudin, (b) allow bivalirudin salt to dissolve during each step of the process, (c) avoid the formation of a bivalirudin precipitate, and (d) control the generation of Asp$^9$-bivalirudin and other impurities.

Example 4

Concentrated liquid bivalirudin drug product and lyophilized bivalirudin drug product were prepared using aqueous solutions comprising acetate buffer (0.25 M), citrate buffer (0.25 M), succinate buffer (0.25 M), or bicarbonate buffer (0.25 M) to determine whether aqueous solutions having a starting pH greater than one unit above the pK$_a$ of the buffer may affect the generation of impurities during the method for preparing bivalirudin drug product. The study also investigated whether these buffers prevent the formation of a bivalirudin precipitate and allow the solid bivalirudin salt to dissolve.

A. Acetate Buffer at pH 6.3

An aqueous solution comprising sodium acetate buffer (0.25 M) was prepared by adding 1.6634 g of sodium acetate trihydrate to 35 mL of sterile WFI, followed by the addition of 0.0210 g of glacial acetic acid. The pH was adjusted to 6.27 by the addition of 0.04 mL of 1 N sodium hydroxide. Mannitol was added (1.2601 g) with stirring to the aqueous solution. Solid bivalirudin salt (2.8201 g) was slowly added and stirred until the bivalirudin salt dissolved (about 25 minutes). No bivalirudin precipitate was observed during the formation of the bulk solution. The pH of the resulting bulk solution was 4.79. Sterile WFI was added (q.s.) with stirring to obtain a total volume of 50 mL. The final bivalirudin concentration of the bulk solution was about 50 mg/mL.

B. Succinate Buffer at pH 6.3

An aqueous solution comprising succinate buffer (0.25 M) was prepared by adding 0.0419 g of succinic acid to 35 mL of sterile WFI, followed by the addition of 1.2038 g of disodium succinate. The pH was adjusted to 6.34 by the addition of 0.2 g of 1 N sodium hydroxide. Mannitol was added (1.2601 g) with stirring to the aqueous solution. Solid bivalirudin salt (2.8206 g) was slowly added and stirred until the bivalirudin salt dissolved (about 25 minutes). No bivalirudin precipitate was observed during the formation of the bulk solution. The pH of the resulting bulk solution was 4.95. Sterile WFI was added (q.s.) to obtain a total volume of 50 mL. The final bivalirudin concentration of the bulk solution was about 50 mg/mL.

C. Acetate Buffer at pH 8.0

An aqueous solution comprising acetate buffer (0.25 M) was prepared by adding 1.6998 g of sodium acetate trihydrate to 35 mL of sterile WFI, followed by the addition of 0.4 mg of glacial acetic acid. The pH was adjusted to 8.01 by the addition of 0.08 g of 1 N sodium hydroxide. Mannitol was added (1.2604 g) with stirring to the aqueous solution. Solid bivalirudin salt (2.8209 g) was slowly added and stirred until bivalirudin salt dissolved (about 25 minutes). No bivalirudin precipitate was observed during the formation of the bulk solution. The pH of the resulting bulk solution was 4.89 and was adjusted to 5.09 by the addition of 2.3 g of 1 N sodium hydroxide. Sterile WFI was added (q.s.) to obtain a total volume of 50 mL. The final bivalirudin concentration of the bulk solution was about 50 mg/mL.

D. Bicarbonate Buffer at pH 7.9

An aqueous solution comprising bicarbonate buffer (0.25 M) was prepared by adding 1.0404 g of sodium bicarbonate to 35 mL of sterile WFI. The pH was adjusted to 7.89 by the addition of 0.12 g of 1 N HCl. Mannitol was added (1.2603 g) with stirring to the aqueous solution. Solid bivalirudin salt (2.8202 g) was slowly added and stirred until bivalirudin salt dissolved (about 25 minutes). No bivalirudin precipitate was observed during the formation of the bulk solution. The pH of the resulting bulk solution was 7.45. Sterile WFI was added (q.s.) to obtain a total volume of 50 mL, and the pH was 7.95. The final bivalirudin concentration of the bulk solution was about 50 mg/mL.

E. Purity Determinations

Each of the bulk solutions described above (4A-4D) was sterile filtered (0.22-μm Durapore Membrane) and divided into 5 mL portions that were transferred into glass vials and stoppered. One vial was stored at ambient temperature and another vial was stored at 40° C. for seven days (i.e., liquid bivalirudin concentrate drug product), while the remaining vials were stored at −20° C. All the frozen vials were lyophilized except one vial, which remained frozen until analyzed (i.e., liquid bivalirudin concentrate drug product, t=0). Purity determinations for the lyophilized and liquid concentrate drug products are presented in Tables 7-8, and 9-10 respectively, where the values are measurements from a single vial using the same HPLC conditions as shown in Example 3D.

TABLE 7

Determination of Bivalirudin Purity in a Lyophilized Drug Product.

| Buffer (pK$_a$) | Initial pH | Final pH[1] | Change in Asp$^9$ (%)[2] | Final Asp$^9$ (%) | Total Impurity (%) |
|---|---|---|---|---|---|
| Acetate (4.8) | 6.37 | 4.79 | 0 | 0.4 | 1.5 |
| Succinate (4.2, 5.6) | 6.34 | 4.95 | 0 | 0.4 | 1.3 |
| Acetate (4.8) | 8.01 | 5.09 | 0 | 0.3 | 0.9 |
| Bicarbonate (6.4) | 7.89 | 7.45 | 17.1 | 17.3 | 21.7 |

[1]The initial pH refers to the pH of the aqueous solution. The final pH refers to the pH of the bulk solution after bivalirudin salt addition (before any pH adjustment).
[2]The change in Asp$^9$-bivalirudin refers to the difference in Asp$^9$-bivalirudin between the drug substance and the final drug product (t = 0). As such, the change in Asp$^9$-bivalirudin measured in the liquid concentrate or lyophilized drug products is representative of Asp$^9$-bivalirudin generated during the formation of the bulk solution.

TABLE 8

Determination of Bivalirudin Purity in a Lyophilized Drug Product.

| Buffer (pK$_a$) | [9-10]-cyclo (%)[1] | [1-11]-Bvl (%) | [12-20]-Bvl (%) | [3-20]-Bvl (%) | [11-12]-cyclo (%) |
|---|---|---|---|---|---|
| Acetate (4.8) | 0.1 | 0.1 | 0.3 | 0.1 | 0.1 |
| Succinate (4.2, 5.6) | 0.1 | 0.1 | 0.3 | 0.1 | 0.1 |
| Acetate (4.8) | 0.1 | 0.1 | 0.2 | 0.1 | 0 |
| Bicarbonate (6.4) | 1.3 | 0.1 | 0.2 | 1.7 | 0 |

[1]Contains minor co-eluting D-Phe$^{12}$ impurity.

TABLE 9

Determination of Bivalirudin Purity in the Concentrated Drug Product at t = 0 and 7 days at ambient temperature.

| Buffer (pKa) | Initial pH | Final pH[1] | Days | Change in Asp$^9$ (%)[2] | Final Asp$^9$ (%) | Total Impurity (%) |
|---|---|---|---|---|---|---|
| Acetate (4.8) | 6.37 | 4.79 | 0 | 0 | 0.4 | 1.4 |
|  |  |  | 7 | 0 | 0.4 | 3.6 |
| Succinate (4.2, 5.6) | 6.34 | 4.95 | 0 | 1.7 | 2.2 | 3.5 |
|  |  |  | 7 | 0 | 0.4 | 3.1 |
| Acetate (4.8) | 8.01 | 5.09 | 0 | 0 | 0.3 | 1.0 |
|  |  |  | 7 | 0 | 0.4 | 3.3 |
| Bicarbonate (6.4) | 7.89 | 7.45 | 0 | 19.4 | 19.6 | 23.6 |
|  |  |  | 7 | 65.5 | 65.7 | 95.6 |

[1]The initial pH refers to the pH of the aqueous solution. The final pH refers to the pH of the bulk solution after bivalirudin salt addition (before any pH adjustment).
[2]The change in Asp$^9$-bivalirudin refers to the difference in Asp$^9$-bivalirudin between the drug substance and the final drug product (t = 0). As such, the change in Asp$^9$-bivalirudin measured in the liquid concentrate or lyophilized drug products is representative of Asp$^9$-bivalirudin generated during the formation of the bulk solution.

TABLE 10

Determination of Bivalirudin Purity in a Concentrated Drug Product at t = 0 and 7 days at ambient temperature.

| Buffer (pK$_a$) | Days | [9-10]-cyclo (%)[1] | [1-11]-Bvl (%) | [12-20]-Bvl (%) | [3-20]-Bvl (%) | [11-12]-cyclo (%) |
|---|---|---|---|---|---|---|
| Acetate (4.8) | 0 | 0.1 | 0.2 | 0.3 | 0.1 | 0.1 |
|  | 7 | 0.5 | 0.3 | 0.4 | 0.9 | 0.6 |
| Succinate (4.2, 5.6) | 0 | 0.1 | 0.2 | 0.2 | 0.1 | 0.1 |
|  | 7 | 0 | 0.3 | 0.4 | 1.0 | 0.5 |

TABLE 10-continued

Determination of Bivalirudin Purity in a Concentrated Drug Product at t = 0 and 7 days at ambient temperature.

| Buffer (pK$_a$) | Days | [9-10]-cyclo (%)[f] | [1-11]-Bvl (%) | [12-20]-Bvl (%) | [3-20]-Bvl (%) | [11-12]-cyclo (%) |
|---|---|---|---|---|---|---|
| Acetate (4.8) | 0 | 0.1 | 0.1 | 0.2 | 0.1 | 0.1 |
|  | 7 | 0 | 0 | 0.2 | 1.0 | 0.4 |
| Bicarbonate (6.4) | 0 | 0.8 | 0.1 | 0.1 | 1.7 | 0 |
|  | 7 | 0 | 0.2 | 0.3 | 1.1 | 0 |

[1]Contains minor co-eluting D-Phe[12] impurity.

The results suggest that buffers having a pK$_a$ ranging from 4.2 to 6.4 are well suited to (a) maintain the pH of bulk solutions (containing approximately 50 mg/mL of bivalirudin) above the pI of bivalirudin, (b) allow bivalirudin salt to dissolve during each step of the process, and (c) avoid the formation of a bivalirudin precipitate. The results also suggest that a final pH of 7.45 is not suitable to control the generation of Asp$^9$-bivalirudin and other impurities.

Example 5

A bulk solution was prepared using an aqueous solution comprising an acetate buffer to determine the effects of adding bivalirudin salt to the aqueous solution in a first portion, adjusting the pH of the bulk solution, and then adding bivalirudin salt in a second portion.

An aqueous solution comprising an acetate buffer (0.1 M) was prepared by the addition of 0.28 g of sodium acetate trihydrate to 17.5 mL of sterile WFI. Glacial acetic acid (0.03 g) was added with stirring, and the resulting pH was 5.25. A first portion of bivalirudin salt (0.705 g) was slowly added with stirring until bivalirudin salt was completely dissolved (approximately 25 minutes), resulting in a bulk solution. No bivalirudin precipitate was observed during the formation of the bulk solution. The pH of the bulk solution was adjusted from 4.43 to 5.21 by the slow addition of 1.44 g of 1 N sodium hydroxide with stirring. A second portion of bivalirudin salt (0.705 g) was slowly added with stirring to the bulk solution and stirring continued until bivalirudin salt was completely dissolved (approximately 30 minutes). No bivalirudin precipitate was observed during the formation of the bulk solution. The resulting pH of the bulk solution was 4.59. Mannitol (0.63 g) was then added with stirring and 2.36 g of 1 N sodium hydroxide was added to adjust the pH to 5.23. Sterile WFI was added (q.s.) to give a total volume of 25 mL. The final bivalirudin and mannitol concentrations were about 50 mg/mL and about 25 mg/mL, respectively.

These results suggest that bivalirudin salt can be added portion-wise with pH adjustments to an aqueous solution comprising a 0.1 M acetate buffer to allow bivalirudin salt to (a) rapidly dissolve and (b) avoid the formation of a bivalirudin precipitate.

Example 6

Base was added to a bivalirudin salt solution to confirm the formation of a bivalirudin precipitate as the pH of the solution passes through the pI of bivalirudin.

Solid bivalirudin salt (2.0 g) was added to 40 mL of sterile WFI to form a bivalirudin salt solution having a pH of 1.81. Sodium hydroxide (1 N) was added drop-wise to the bivalirudin salt solution and the pH was monitored. Qualitative observations were recorded for the precipitate that formed, as described in Table 11.

TABLE 11

Qualitative Observations During the Addition of Base to a Bivalirudin Salt Solution.

| pH after addition of NaOH | Observations |
|---|---|
| 1.9-2.9 | Bivalirudin salt solution was initially clear. Cloudiness (localized precipitation) was observed immediately following drop-wise addition of NaOH. Cloudiness was dispersed during stirring, and a clear solution was observed. |
| 3.0-3.5 | Bivalirudin salt solution became cloudy after drop-wise addition of NaOH. Cloudiness was not dispersed during stirring and a cloudy solution remained. |
| 3.6-3.9 | "Gum-like" material was observed in the bivalirudin salt solution. The bivalirudin salt solution was becoming clear but the "gum-like" material was sticking to the glassware. |
| 3.9-5.3 | Bivalirudin salt solution was clear but the "gum-like" material continued to stick to the glassware. |

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for preventing the formation of a bivalirudin precipitate and controlling generation of $Asp^9$-bivalirudin during preparation of a pharmaceutical drug product comprising about 250 mg of bivalirudin, wherein the method comprises:
   (i) preparing an aqueous solution comprising (a) a buffer having a $pK_a$ of about 4 to about 6, and (b) a pH greater than the isoelectric point of bivalirudin;
   (ii) adding bivalirudin salt to the aqueous solution to form a bulk solution, wherein (a) the pH of the bulk solution is maintained at a level greater than the isoelectric point of bivalirudin, and (b) the bulk solution has a final pH of between 5 and about 6;
   (iii) transferring the bulk solution to one or more vessels such that each vessel contains about 250 mg of bivalirudin;
   (iv) drying the bulk solution to obtain a pharmaceutical drug product; and
   (v) measuring $Asp^9$-bivalirudin levels, wherein zero $Asp^9$-bivalirudin, as measured by high performance liquid chromatography at 215 nm, is generated during the method.

2. The method of claim 1, wherein the aqueous solution comprises two or more buffers.

3. The method of claim 1, wherein the buffer has a $pK_a$ of about 4.5 to about 6.

4. The method of claim 3, wherein the buffer has a $pK_a$ of about 4.8.

5. The method of claim 1, wherein the buffer comprises a concentration of about 0.1 M to about 2 M.

6. The method of claim 5, wherein the buffer comprises a concentration of about 0.1 M to about 0.5 M.

7. The method of claim 1, wherein the aqueous solution comprises a pH greater than the isoelectric point of bivalirudin and less than 10.

8. The method of claim 7, wherein the aqueous solution comprises a pH of about 5 to about 8.

9. The method of claim 1, wherein bivalirudin salt is added to the aqueous solution continuously or intermittently in two or more portions to form the bulk solution.

10. The method of claim 9, further comprising adding a base to the bulk solution during or after the addition of bivalirudin salt.

11. The method of claim 1, wherein the bivalirudin salt is a solid.

12. The method of claim 1, wherein the bulk solution has a final concentration of about 25 mg/mL to about 100 mg/mL.

13. The method of claim 12, wherein the bulk solution has a final concentration of about 50 mg/mL.

14. The method of claim 1, further comprising adding one or more pharmaceutically acceptable excipients to the aqueous solution, to the bulk solution, or a combination thereof.

15. The method of claim 14, wherein the pharmaceutically acceptable excipient is mannitol.

16. The method of claim 1, further comprising sterilizing the bulk solution before drying the bulk solution.

17. The method of claim 1, wherein drying the bulk solution comprises lyophilizing.

* * * * *